United States Patent
Strausbaugh et al.

(10) Patent No.: US 8,100,946 B2
(45) Date of Patent: Jan. 24, 2012

(54) POLYAXIAL BONE ANCHORS WITH INCREASED ANGULATION

(75) Inventors: William L. Strausbaugh, Leola, PA (US); Sean Saidha, East Fallowfield, PA (US); Boyd A. Wolf, Coatesville, PA (US)

(73) Assignee: Synthes USA, LLC, West Chester, PA (US)

( * ) Notice: Subject to any disclaimer, the term of this patent is extended or adjusted under 35 U.S.C. 154(b) by 652 days.

(21) Appl. No.: 11/603,428

(22) Filed: Nov. 21, 2006

(65) Prior Publication Data
US 2007/0118123 A1   May 24, 2007

Related U.S. Application Data

(60) Provisional application No. 60/739,100, filed on Nov. 21, 2005.

(51) Int. Cl.
*A61B 17/70*   (2006.01)
(52) U.S. Cl. ......... 606/266; 606/268; 606/269; 606/270
(58) Field of Classification Search .................. 606/246, 606/264–279
See application file for complete search history.

(56) References Cited

U.S. PATENT DOCUMENTS

| | | |
|---|---|---|
| 2,005,348 A | 6/1935 | Michell |
| 4,601,491 A | 7/1986 | Bell, Jr. et al. |
| 4,805,602 A | 2/1989 | Puno |
| 4,846,614 A | 7/1989 | Steinbock |
| 5,005,562 A | 4/1991 | Cotrel |
| 5,129,388 A | 7/1992 | Vignaud |
| 5,207,678 A | 5/1993 | Harms |
| 5,360,431 A | 11/1994 | Puno |
| 5,413,602 A | 5/1995 | Metz-Stavenhagen |
| 5,443,467 A | 8/1995 | Biedermann |
| 5,466,237 A | 11/1995 | Byrd |
| 5,468,241 A | 11/1995 | Metz-Stavenhagen |
| 5,474,555 A | 12/1995 | Puno |
| 5,476,464 A | 12/1995 | Metz-Stavenhagen |
| 5,496,321 A | 3/1996 | Puno |
| 5,536,268 A | 7/1996 | Griss |
| 5,586,984 A | 12/1996 | Errico |
| 5,605,457 A | 2/1997 | Bailey et al. |
| 5,605,458 A | 2/1997 | Bailey |

(Continued)

FOREIGN PATENT DOCUMENTS

DE   29903342   6/1999

(Continued)

*Primary Examiner* — Eduardo C Robert
*Assistant Examiner* — Steven Controneo
(74) *Attorney, Agent, or Firm* — Woodcock Washburn LLP

(57) ABSTRACT

A polyaxial bone anchor includes an anchor head, an anchor member, a bushing, a sleeve and a fastener. The anchor head has a longitudinal bore and an inner spherical surface on a lower portion. The bushing is received within the longitudinal bore adjacent the lower portion and includes an exterior spherical surface for interacting with the inner spherical surface in the anchor head, an internal space defining an inner spherical surface for mating with a spherical head portion of the anchor member and a slot. The inner spherical surface of the bushing has a spherical centerpoint and the exterior spherical surface of the bushing has a spherical centerpoint. The spherical centerpoint of the inner spherical surface is vertically displaced toward the bottom end relative to the spherical centerpoint of the exterior spherical surface. The sleeve is received within the longitudinal bore. The fastener is mountable to the anchor head.

67 Claims, 6 Drawing Sheets

U.S. PATENT DOCUMENTS

| | | | |
|---|---|---|---|
| 5,607,304 | A | 3/1997 | Bailey |
| 5,624,442 | A | 4/1997 | Mellinger |
| 5,643,262 | A | 7/1997 | Metz-Stavenhagen |
| 5,647,873 | A | 7/1997 | Errico |
| 5,667,508 | A | 9/1997 | Errico |
| 5,669,911 | A | 9/1997 | Errico |
| 5,683,390 | A | 11/1997 | Metz-Stavenhagen |
| 5,690,630 | A | 11/1997 | Errico |
| 5,728,098 | A | 3/1998 | Sherman |
| 5,738,685 | A | 4/1998 | Halm et al. |
| 5,782,833 | A | 7/1998 | Haider |
| 5,797,911 | A | 8/1998 | Sherman |
| 5,810,818 | A | 9/1998 | Errico et al. |
| 5,817,094 | A | 10/1998 | Errico et al. |
| 5,879,350 | A | 3/1999 | Sherman |
| 5,882,350 | A * | 3/1999 | Ralph et al. .................. 606/278 |
| 5,885,286 | A | 3/1999 | Sherman |
| 5,964,760 | A | 10/1999 | Richelsoph |
| 6,001,098 | A | 12/1999 | Metz-Stavenhagen |
| 6,010,503 | A | 1/2000 | Richelsoph |
| 6,019,760 | A | 2/2000 | Metz-Stavenhagen |
| 6,053,917 | A | 4/2000 | Sherman |
| 6,063,090 | A | 5/2000 | Schlapfer |
| 6,074,391 | A | 6/2000 | Metz-Stavenhagen |
| 6,090,110 | A | 7/2000 | Metz-Stavenhagen |
| 6,132,432 | A | 10/2000 | Richelsoph |
| 6,183,472 | B1 | 2/2001 | Lutz |
| 6,214,006 | B1 | 4/2001 | Metz-Stavenhagen |
| 6,224,598 | B1 | 5/2001 | Jackson |
| 6,261,287 | B1 | 7/2001 | Metz-Stavenhagen |
| 6,280,442 | B1 | 8/2001 | Barker |
| 6,296,642 | B1 | 10/2001 | Morrison |
| 6,355,040 | B1 * | 3/2002 | Richelsoph et al. .......... 606/272 |
| 6,361,535 | B2 | 3/2002 | Jackson |
| RE37,665 | E | 4/2002 | Ralph |
| 6,443,953 | B1 | 9/2002 | Perra |
| 6,451,021 | B1 | 9/2002 | Ralph |
| 6,454,768 | B1 | 9/2002 | Jackson |
| 6,471,705 | B1 * | 10/2002 | Biedermann et al. ......... 606/271 |
| 6,482,207 | B1 | 11/2002 | Errico |
| 6,485,491 | B1 | 11/2002 | Farris |
| 6,508,820 | B2 | 1/2003 | Bales |
| 6,520,963 | B1 * | 2/2003 | McKinley ..................... 606/266 |
| 6,537,276 | B2 | 3/2003 | Metz-Stavenhagen |
| 6,565,565 | B1 | 5/2003 | Yuan |
| 6,626,908 | B2 | 9/2003 | Cooper |
| 6,641,586 | B2 | 11/2003 | Varieur |
| 6,660,004 | B2 | 12/2003 | Barker |
| 6,726,687 | B2 | 4/2004 | Jackson |
| 6,740,086 | B2 | 5/2004 | Richelsoph |
| 6,755,829 | B1 | 6/2004 | Bono |
| 6,783,527 | B2 | 8/2004 | Drewry |
| 6,835,196 | B2 | 12/2004 | Biedermann |
| 6,840,940 | B2 | 1/2005 | Ralph |
| 6,843,791 | B2 | 1/2005 | Serhan |
| 6,869,433 | B2 | 3/2005 | Glascott |
| 6,981,973 | B2 | 1/2006 | McKinley |
| 7,018,378 | B2 | 3/2006 | Biedermann |
| RE39,089 | E | 5/2006 | Ralph |
| 7,081,117 | B2 | 7/2006 | Bono |
| 7,087,057 | B2 | 8/2006 | Konieczynski |
| 7,125,426 | B2 | 10/2006 | Moumene |
| 7,128,743 | B2 | 10/2006 | Metz-Stavenhagen |
| 7,144,396 | B2 | 12/2006 | Shluzas |
| 7,223,268 | B2 | 5/2007 | Biedermann |
| 7,591,839 | B2 * | 9/2009 | Biedermann et al. ......... 606/266 |
| 2002/0120272 | A1 | 8/2002 | Yuan |
| 2002/0143341 | A1 | 10/2002 | Biedermann |
| 2003/0100896 | A1 | 5/2003 | Biedermann |
| 2003/0100904 | A1 | 5/2003 | Biedermann |
| 2003/0125741 | A1 | 7/2003 | Biedermann |
| 2003/0125742 | A1 | 7/2003 | Yuan |
| 2003/0149431 | A1 | 8/2003 | Varieur |
| 2004/0138660 | A1 | 7/2004 | Serhan |
| 2004/0153077 | A1 | 8/2004 | Biedermann |
| 2004/0181224 | A1 | 9/2004 | Biedermann |
| 2004/0186473 | A1 | 9/2004 | Cournoyer |
| 2004/0186474 | A1 | 9/2004 | Matthis |
| 2004/0193160 | A1 | 9/2004 | Richelsoph |
| 2004/0249380 | A1 | 12/2004 | Glascott |
| 2005/0080415 | A1 * | 4/2005 | Keyer et al. .................... 606/61 |
| 2005/0154391 | A1 * | 7/2005 | Doherty et al. ................. 606/61 |
| 2005/0171542 | A1 | 8/2005 | Biedermann |
| 2005/0187548 | A1 | 8/2005 | Butler |
| 2005/0203515 | A1 | 9/2005 | Doherty |
| 2005/0203516 | A1 * | 9/2005 | Biedermann et al. ........... 606/61 |
| 2005/0228385 | A1 | 10/2005 | Lott |
| 2005/0277928 | A1 | 12/2005 | Boschert |
| 2005/0288671 | A1 | 12/2005 | Yuan |
| 2006/0004357 | A1 | 1/2006 | Lee |
| 2006/0025767 | A1 | 2/2006 | Khalili |
| 2006/0084995 | A1 | 4/2006 | Biedermann |
| 2006/0084996 | A1 | 4/2006 | Metz-Stavenhagen |
| 2006/0089643 | A1 | 4/2006 | Mujwid |
| 2006/0106383 | A1 | 5/2006 | Biedermann |
| 2006/0129149 | A1 | 6/2006 | Lott |
| 2006/0149232 | A1 | 7/2006 | Sasing |
| 2006/0149233 | A1 | 7/2006 | Richelsoph |
| 2006/0149241 | A1 | 7/2006 | Richelsoph |
| 2006/0155277 | A1 | 7/2006 | Metz-Stavenhagen |
| 2006/0200131 | A1 | 9/2006 | Chao |
| 2006/0217717 | A1 | 9/2006 | Whipple |
| 2006/0235385 | A1 | 10/2006 | Whipple |
| 2006/0235393 | A1 | 10/2006 | Bono |
| 2006/0241599 | A1 | 10/2006 | Konieczynski |
| 2006/0247636 | A1 | 11/2006 | Yuan |
| 2007/0118118 | A1 | 5/2007 | Kwak |

FOREIGN PATENT DOCUMENTS

| | | |
|---|---|---|
| DE | 29810798 | 10/1999 |
| DE | 19912364 | 10/2000 |
| EP | 1210914 | 5/2002 |
| JP | 8112291 | 5/1996 |

* cited by examiner

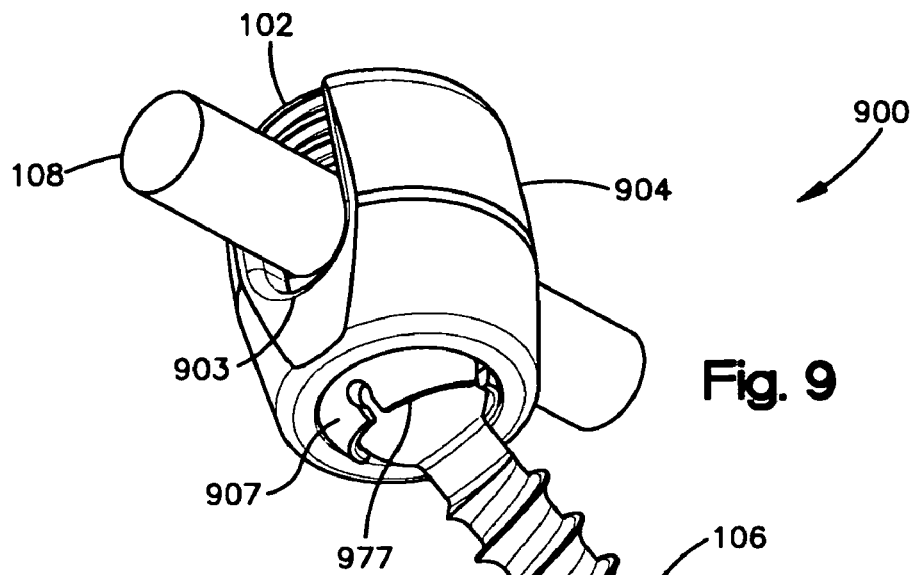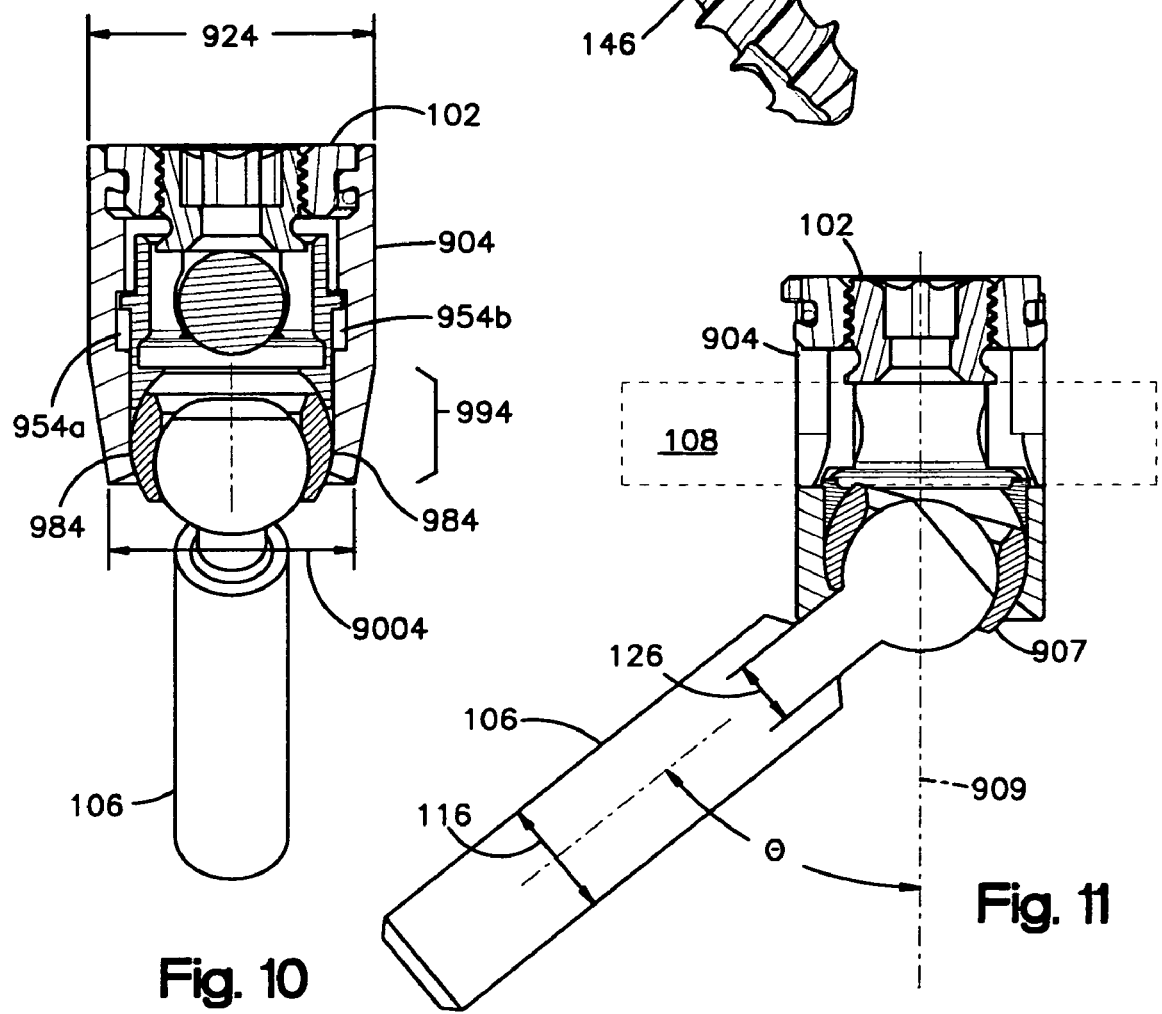

US 8,100,946 B2

POLYAXIAL BONE ANCHORS WITH INCREASED ANGULATION

CROSS REFERENCE TO RELATED APPLICATION

This claims the benefit of U.S. Provisional Application No. 60/739,100, filed Nov. 21, 2005.

TECHNICAL FIELD OF THE INVENTION

This invention relates to bone fixation devices and related methods of fixation. More particularly, this invention relates to polyaxial bone anchors, such as pedicle screws and hooks, having increased angulation for use in, for example, the posterior fixation of the spine.

BACKGROUND OF THE INVENTION

Polyaxial bone anchors and methods of use in treating spinal disorders are known. Typical methods involve anchoring at least two screws or hooks into the vertebrae, and fixing the screws or hooks along a spinal rod to position or immobilize the vertebrae with respect to one another. The screws or hooks commonly have anchor heads with U-shaped channels in which the spinal rod is inserted and subsequently clamped by a fastener, such as, for example, a threaded nut, set screw, or locking cap. These methods commonly involve multiple screws or hooks and multiple spinal rods. The spinal rod(s) may be shaped to maintain the vertebrae in a desired orientation so as to correct the spinal disorder at hand (e.g., to straighten a spine having abnormal curvature). Additionally or alternatively, the screws or hooks may be spaced along the rods(s) to compress or distract adjacent vertebrae.

Surgeons may encounter difficulty with spinal fixation and stabilization methods because of difficulty aligning the spinal rod(s) with the U-shaped channels in the anchor heads of the screws or hooks. For example, the anchor heads are often out of alignment with one another because of the curvature of the spine or the size and shape of each vertebrae. To facilitate easier insertion of the spinal rods into the U-shaped channels, and to provide additional flexibility in the positioning of the spinal rods and the screws and hooks, bone anchors have been developed where the anchor member (e.g., screw or hook) and anchor head can initially pivot or rotate with respect to each other. These bone anchors are sometimes referred to as polyaxial bone anchors and the pivot or rotation of the anchor member is referred to as angulation.

A disadvantage of many polyaxial bone anchors is the degree to which the anchor head and member can angulate. Typical polyaxial bone anchors have anchor members that can rotate up to about 30° from a central axis extending down through the anchor head. It may be advantageous to provide polyaxial bone anchors with increased angulation.

SUMMARY OF THE INVENTION

The invention is directed to polyaxial bone anchors and methods of use for attaching a rod, such as a support or spinal rod, to a bone, such as a vertebra. The bone anchor may include a hollow generally cylindrical housing or head (referred to hereinafter as an anchor head), an optional hollow generally cylindrical internal sleeve, an internal locking element, a pedicle screw (or other type of anchor member, such as, for example, a hook or other similar structure), and preferably a locking cap with set screw (alternatively, other types of fasteners and fastening arrangements, such as, for example, a threaded nut or locking sleeve mounted on or over the top portion of the head, are also within the scope of the invention). The anchor head and internal sleeve may have a U-shaped channel for receiving a support/spinal rod (referred to hereinafter as a spinal rod or rod). The locking element preferably is sized and shaped to snap on to the head of the pedicle screw. And the locking cap and set screw may close the top opening of the U-shaped channel after a rod has been placed therein and, in combination with the locking element, lock or clamp the respective positions of the pedicle screw and rod.

The anchor head, the internal sleeve, and primarily the locking element have features that allow the locking element to rotate or pivot within the anchor head. This in turn allows the pedicle screw to rotate or pivot around and away from the central axis of the anchor head at large angles. The pedicle screw or hook may be locked with respect to the anchor head at these large angles. The angulation is preferably as much as about 50° in every direction from the central axis. This advantageously provides greater flexibility to the surgeon when aligning spinal rods with the anchor heads of implanted screws and hooks during surgery.

In one embodiment of the invention, the locking element, which can be described as a collet or collet-style bushing, has an upper portion with a plurality of resilient tabs to initially receive and hold the head of a pedicle screw. The internal sleeve has a bottom surface with a preferably corresponding inward taper to mate with the tapered shape of the exterior surface of the tabs on the collet to allow rotation and facilitate locking of the collet. The collet has at least one cutout of preferably about 50° on its lower side and the anchor head has a lower portion with a tapered inner surface that together make possible the large angulation of the pedicle screw mounted in the collet. The anchor head preferably also has an internal ledge for receiving a corresponding lip or projection on the collet to seat it within the head and allow it to rotate about the longitudinal axis of the bore of the anchor head so the cutout can be aligned in a desired direction for full angulation of the pedicle screw. The collet may have one or more cutouts and preferably has multiple cutouts. When the bone anchor is ready to be locked, the bottom interior surface of the internal sleeve presses down on the outside of the tabs of the collet so that the collet compresses around the screw head to lock the position of the screw.

In another embodiment of the invention, the locking element, which may be described as a spherical bushing, can rotate or swivel within the anchor head prior to locking. The anchor head has a lower portion with a spherically-cut inner surface that facilitates rotation of the spherical bushing about a point within the anchor head. The spherical bushing has a spherical exterior shape, a spherical interior shape, and preferably at least one slot that permits the bushing to compress the head of a pedicle screw or hook inserted into the interior of the spherical bushing. Preferably, the pedicle screw or hook has an arcuate or spherical upper portion (head) whose shape corresponds to the interior shape of the spherical bushing. The internal sleeve has a bottom interior surface with a spherical shape to mate with the exterior spherical shape of the top portion of the spherical bushing. The interior surface of the spherical bushing has a centerpoint that is preferably offset from the centerpoint of the exterior surface of the spherical bushing and hence the pedicle screw mounted within it. This offset provides additional angulation as follows: The pedicle screw angulates a certain amount before its shank engages an edge of the spherical bushing. The spherical bushing can then rotate with the pedicle screw to provide the additional amount of angulation, the sum of which provides the increased angulation. When the bone anchor is ready to be locked, the internal sleeve is pressed down on the spherical bushing's top surface, so that the bushing compresses around the screw head to lock the position of the screw.

BRIEF DESCRIPTION OF THE DRAWINGS

The detailed description will be better understood in conjunction with the accompanying drawings, in which like reference characters refer to like parts throughout, and in which:

FIGS. 9-11 are perspective, side cross-sectional, and front cross-sectional views, respectively, of a second embodiment of a polyaxial bone anchor;

DETAILED DESCRIPTION OF THE INVENTION

The invention can be used to treat various spinal disorders including, for example, degenerative instabilities and instabilities due to decompression, tumors, infections, and fractures.

Note that while the polyaxial bone anchor is described and illustrated herein with reference to certain preferred or exemplary embodiments, the invention should not be limited to those preferred or exemplary embodiments. Furthermore, the features described and illustrated herein can be used singularly or in combination with other features and embodiments.

Figure 1:
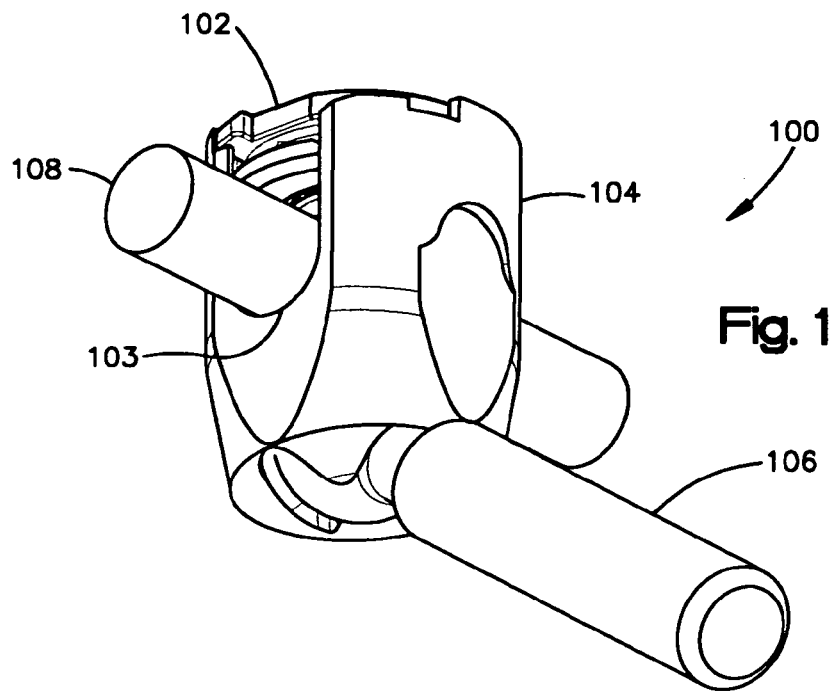
FIGS. 1-3 are perspective, side cross-sectional, and front cross-sectional views, respectively, of a first embodiment of a polyaxial bone anchor.
Figure 2:
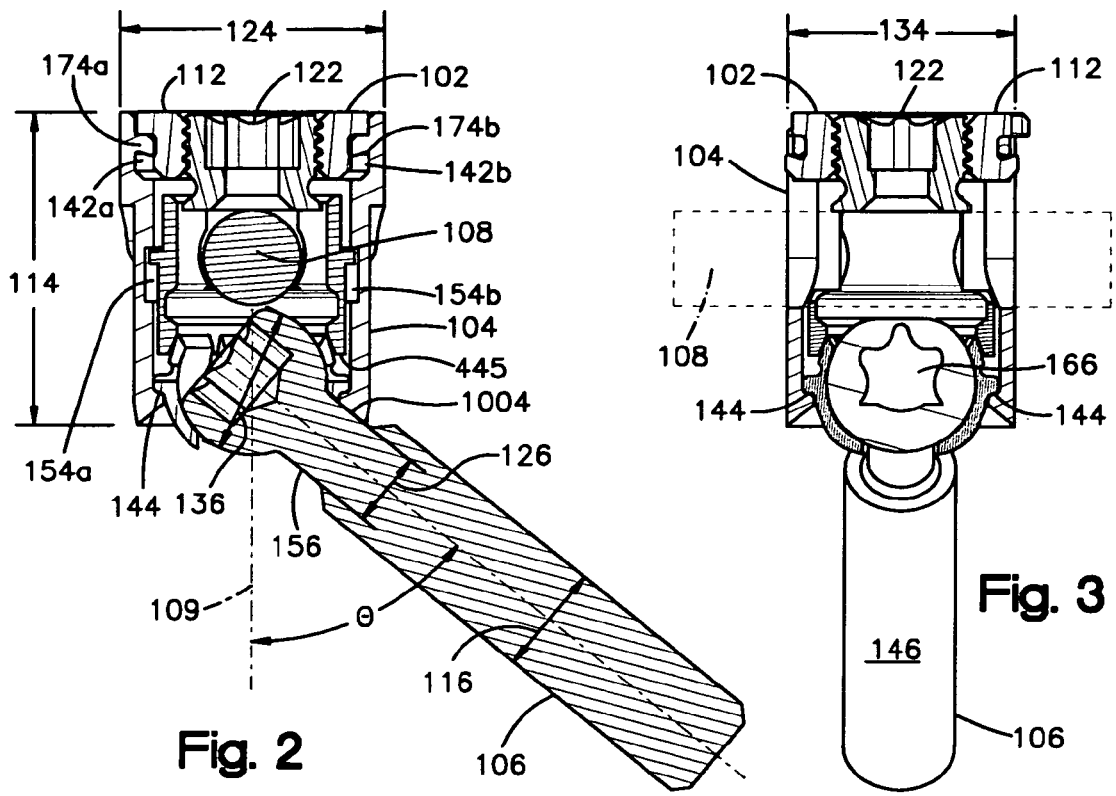
Figure 3:
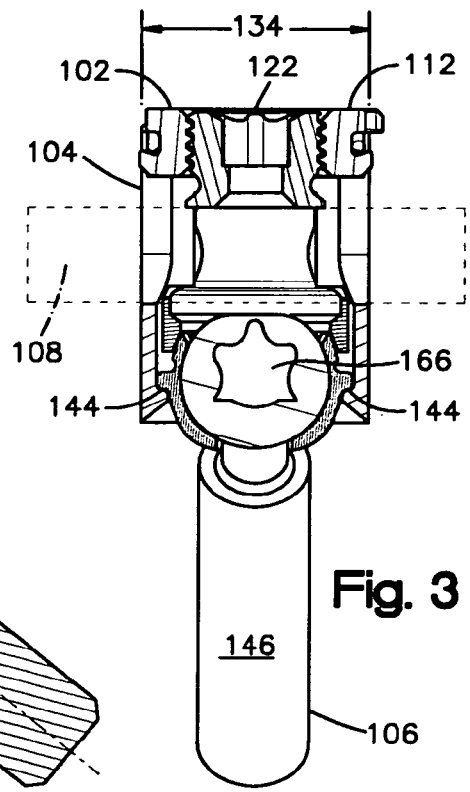

FIGS. 1-3 show a first embodiment of a polyaxial bone anchor. Polyaxial bone anchor 100 includes a fastener 102, an anchor head 104, and an anchor member 106. Fastener 102 is a locking cap that includes a locking ring 112 and a set screw 122 and may be similar or identical to that described in International Patent Application PCT/US2006/015692, internationally filed Apr. 25, 2006, which is incorporated herein by reference in its entirety. Alternatively, fastener 102 may be any known fastener, and anchor head 104 may have any corresponding features required to permit attachment and operation of fastener 102 (e.g., threaded upper arms). Anchor head 104 is preferably cylindrically hollow having a generally longitudinal bore 1014 along longitudinal axis 109. Anchor head 104 also has a generally U-shaped opening 103 transverse to longitudinal bore 1014 for receiving a spinal rod 108 or other similar part. Longitudinal bore 1014 has a top opening 194 and a bottom opening 184. Anchor member 106, which may be a bone or pedicle screw, hook, or other similar structure (and will be referred to hereinafter as pedicle screw 106), extends out of bottom opening 184. Anchor member 106 may be coupled to anchor head 104 such that the head and screw can polyaxially rotate with respect to each other when in an unlocked position, but the angle of the longitudinal axis of anchor member 106 may be fixed with respect to the longitudinal axis of anchor head 104 in a locked position.

One or more polyaxial bone anchors 100 may be attached, for example, to the vertebrae via respective anchor members 106, and a spinal rod 108 or other similar part can be inserted into the U-shaped openings 103. The spinal rod may thereafter be locked with respect to anchor head 104. A system of bone anchors and rods could be used to correctly align the spine or treat other spinal disorders.

Representative dimensions of bone anchor 100 include an anchor head height 114 of about 11.5 mm, a width 124 of about 9.5 mm, and a length 134 of about 8.2 mm. Pedicle screw 106 has a shank diameter 116 of about 4 mm, a neck diameter 126 of about 2.75 mm, and head diameter 136 of about 5.4 mm. Alternatively, bone anchor 100 may be of other dimensions.

Advantageously, pedicle screw 106 can angularly rotate (before being locked or clamped in place) about central axis 109 by an angle θ of preferably about 50° in any direction (i.e., the angular rotation of the head of anchor member 106 in the anchor head forms a cone of preferably about 100°).

Figure 4:
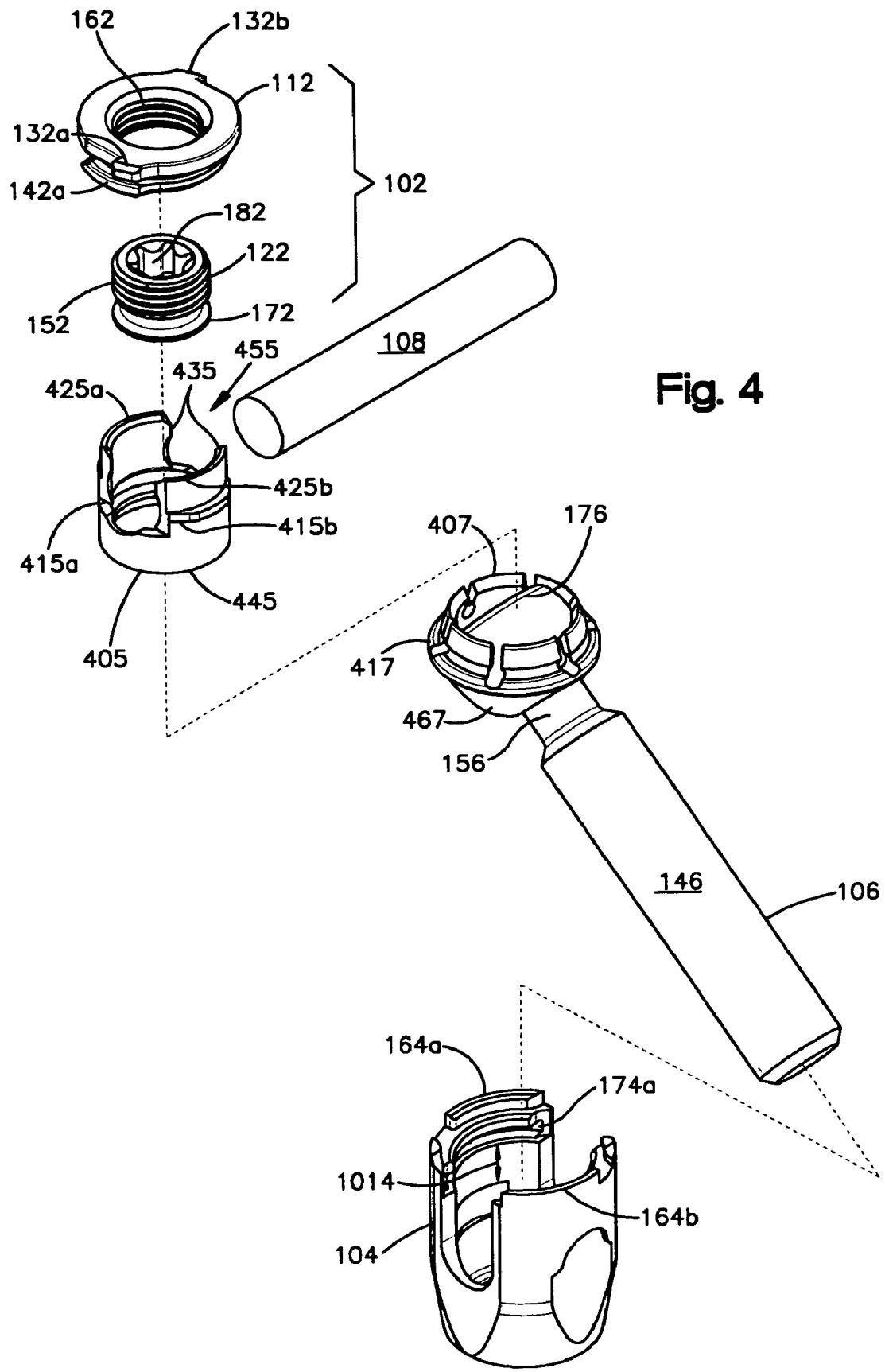
FIG. 4 is an exploded view of the polyaxial bone anchor of FIGS. 1-3.

FIG. 4 shows an exploded view of the assembly of bone anchor 100, which includes locking ring 112 and set screw 122 of locking cap 102, a hollow generally cylindrically shaped internal sleeve 405, a spinal rod 108, an internal locking element 407, a pedicle screw 106 (shown mounted in locking element 407), and an anchor head 104. Bone anchor 100 is first assembled by snap-fitting locking element 407 over the head of pedicle screw 106.

Figure 5A:
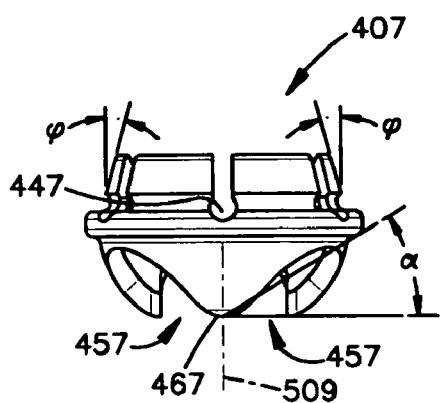
FIGS. 5A and B are elevational views of the locking element of the polyaxial bone anchor of FIGS. 1-4.
Figure 5B:
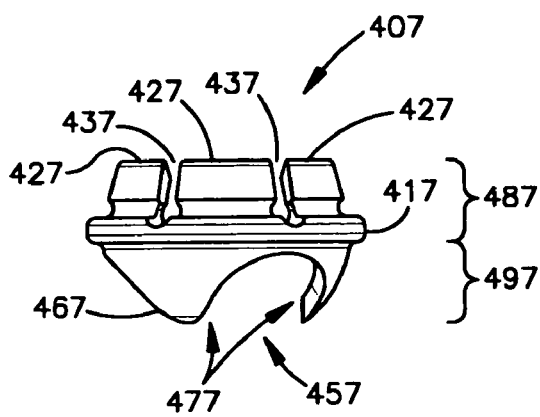

As shown in FIGS. 5A and B, locking element 407 may be described as a collet or collet-styled bushing (referred to hereinafter as collet 407). Collet 407 is made of a resilient material that can be compressed around the head of pedicle screw 106 to retain pedicle screw 106 securely in place. Preferably the material of the collet is softer than the material of internal sleeve 405 and pedicle screw 106.

Figure 6:
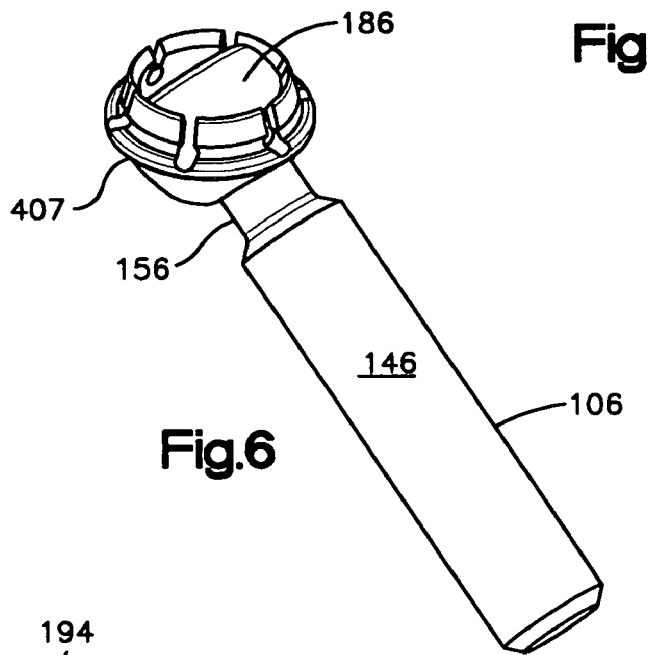
FIG. 6 is a perspective view of the locking element of FIGS. 1-4 with a pedicle screw mounted therein.

Preferably, the upper portion 487 of collet 407 provides the collet with most, if not all, of its screw head retention capabilities. Upper portion 487 has a plurality of resilient tabs 427. The exterior surface of tabs 427 preferably are tapered inward at an angle Φ of preferably about 30°, although other angles Φ are alternatively possible and contemplated. Tabs 427 can deflect outward to allow the head 186 of pedicle screw 106 to be inserted within the internal space of the collet, as shown in FIG. 6. The internal space 477 of collet 407 is shaped to substantially match the shape of the pedicle screw head such that the collet has to be pressed over the screw head in a friction fit. Preferably, the head 186 of the pedicle screw and the internal space of the collet have at least a portion which is spherically shaped. Tabs 427 are separated by slots 437, which may also have a radius or circular shaped portion 447 as a stress relief and/or to provide better resiliency to tabs 427. The arrangement, shapes, and dimensions of the tabs/slots optionally may be different than shown.

Figure 7:
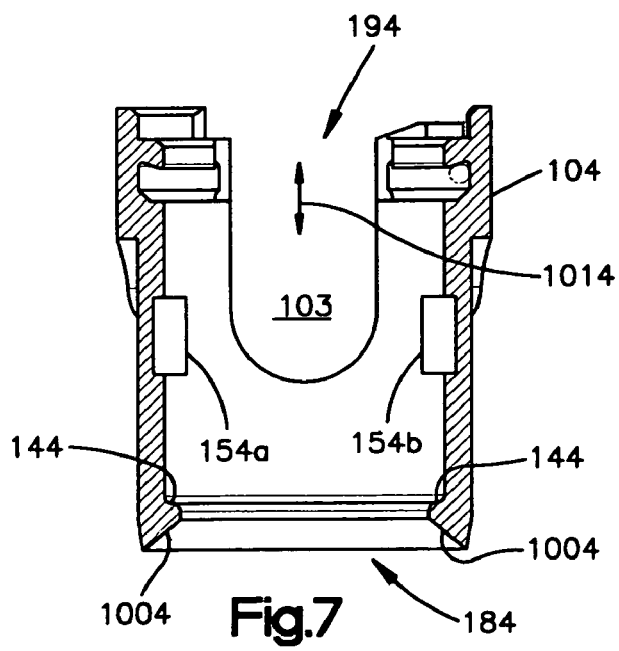
FIG. 7 is a side cross-sectional view of the anchor head of the polyaxial bone anchor of FIGS. 1-4.

The collet/screw assembly is then inserted screw-shank first through the top opening 194 in anchor head 104 until circumferential lip 417 of collet 407 is seated against circumferential internal ledge 144 of anchor head 104 (see FIGS. 2, 3, and 7). Screw shank 146 of pedicle screw 106 now protrudes through the bottom opening 184 of anchor head 104 as shown in FIGS. 1-3. The diameter of collet 407 at lip 417 preferably is such that it can pass through the top opening 194 of anchor head 104, but cannot pass through the bottom opening 184 and more particularly internal ledge 144 of anchor head 104.

The lower portion 497 of collet 407 has one or more cutouts 457 of angle α, which is measured from the bottom of collet 407 at central axis 509 (which coincides with central axis 109 when collet 407 is seated in anchor head 104) to the top of the cutout, as shown in FIG. 5A. Preferably angle α is about 50° (other angles α are alternatively possible). The embodiment of collet 407 shown in FIG. 5A has three 50° cutouts 457. Embodiments with two, four, or more cutouts are possible. Cutouts 457 make possible the larger angulation between the anchor head and pedicle screw where cutouts are located. Collet 407 may rotate or swivel about axis 109 within anchor head 104, prior to the locking of the pedicle screw, to position a cutout in a preferred direction in which to provide full (i.e., maximum) angulation. For example, if a cutout is not aligned as desired, pedicle screw 106 will press against a prong 467 as a surgeon angulates anchor head 104 in a desired direction. This pressing preferably causes collet 407 to rotate within anchor head 104 until cutout 457 is aligned in the desired direction.

The number of cutouts represents a tradeoff between versatility and screw retention capability. That is, a collet with more cutouts has more positions at which to provide full angulation and is thus more easily aligned (i.e., such a collet does not need to be rotated as much to be aligned as a collet with fewer cutouts). However, retention capability (e.g., friction and gripping strength) is in part a function of the amount of surface area in contact with the pedicle screw head. If more area is in contact with the screw head (e.g., because the collet has fewer cutouts), more friction to provisionally hold the pedicle screw in place before locking and more gripping strength to lock the screw in place is available. If more cutouts are provided, less surface area may contact the pedicle screw head, and less friction and gripping strength may be provided.

Also facilitating the angulation of pedicle screw 106 is a preferably tapered lower portion inner surface 1004 of anchor head 104, as shown in FIG. 7. Pedicle screw 106 will angulate until the neck 156 of the screw butts against inner surface 1004, as best shown in FIG. 2.

Internal sleeve 405, which may be optional in some embodiments, is next inserted downward into anchor head 104. Internal sleeve 405 preferably provides a U-shaped channel 455 transverse to a longitudinal bore in sleeve 405. Internal sleeve 405 preferably has a pair of retention tabs 415a,b on its outer surface that snap into respective slots 154a,b on opposite walls of anchor head 104 (best seen in FIG. 2). This aligns the U-shaped channels of anchor head 104 and sleeve 405. Slots 154a,b of anchor head 104 allow sleeve 405 to move up and down from an unlocked screw position to a locked screw position, respectively, on top of collet 407, while retaining the sleeve within the anchor head. Tabs 415a,b may also keep the U-shaped channel in sleeve 405 aligned with the U-shaped opening in the anchor head. Alternatively, other means of keeping U-shaped channel 455 in sleeve 405 aligned with U-shaped opening 103 in anchor head 104 may used, such as, for example, protruding tabs along the boundary of U-shaped channel 455 that project or snap into space provided by the U-shaped opening in anchor head 104.

With fastener 102 removed from the assembly of the anchor head, internal sleeve, collet, and pedicle screw, the pedicle screw may be attached to a bone. The head of pedicle screw 106 preferably has a recess 166 (as shown in FIG. 3) or slot 166 (as shown in FIG. 4) keyed to receive a hex wrench, torque wrench, or other known driver (through the aforementioned assembly) to implant the pedicle screw by rotating into, for example, a vertebra.

Anchor head 104 may now be aligned to receive a rod 108. Rod 108 is preferably snapped into internal sleeve 405. The distance between upright arms 425a,b of sleeve 405 across the narrowest widths 435 of the U-shaped channel is preferably slightly less than the diameter of rod 108. For example, if rod 108 has a diameter of about 3.5 mm, the aforementioned distance would preferably be about 3.26 mm. In this manner, the sleeve may provisionally retain the spinal rod but still permit the rod to slide in the U-shaped channel or be removed. Alternatively or additionally, sleeve 405, with or without the spinal rod, can be pushed down in the anchor head (e.g., by pushing down on the spinal rod in the U-shaped channel) so that the under surface of sleeve 405 interacts with tabs 427 on collet 407 to provisionally lock the pedicle screw with respect to the anchor head. In this manner, the spinal rod is still permitted to slide within and/or be removed from the sleeve.

With the spinal rod in the U-shaped channel (with or without the head of the screw or hook being locked in the anchor head), the locking cap 102 may be placed on anchor head 104, closing the U-shaped channel. In this embodiment, locking cap 102 is first positioned on top of anchor head 104 and pressed downward until it snaps into position. The locking cap is then rotated until oppositely-positioned projections 132a,b on locking ring 112 contact corresponding structures 164a,b, respectively, on anchor head 104. As this occurs, a pair of oppositely-positioned, preferably dovetailed, lateral flanges 142a,b on locking ring 112 slide within corresponding, preferably dovetailed, grooves 174a,b, respectively, on anchor head 104. Preferably, locking ring 112 and the upper surfaces of anchor head 104 do not engage each other with screw threads, although screw threads may be used, as well as different locking caps.

At this stage, rod 108 can still be positioned (e.g., moved) relative to anchor head 104 and pedicle screw 106. Upon satisfactory positioning of the rod and pedicle screw, set screw 122 is driven downward to lock the rod and anchor head in place. Set screw 122 has external threads 152 that mate with internal threads 162 of locking ring 112. Preferably, the set screw is screwed into the locking ring before the locking cap is inserted into the anchor head, and preferably the set screw cannot be screwed out of the locking ring because of a flared portion 172 at the bottom of the set screw. Set screw 122 preferably also has a star socket 182. Alternatively, set screw 122 can have other types of sockets or recesses keyed to other known drivers or tools. A single instrument/tool may be used with locking cap 102 to drive in a single action both locking ring 112 and set screw 122 simultaneously to lock locking cap 102 in place on the anchor head and then to continue driving set screw 122 alone until rod 108 and pedicle screw 106 are clamped in place.

Figure 8:
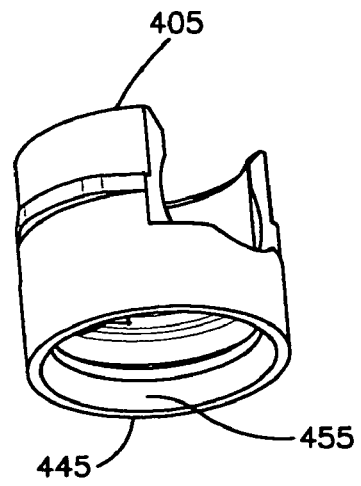
FIG. 8 is a perspective view showing the bottom of the internal sleeve of the polyaxial bone anchor of FIGS. 1-4.

As set screw 122 contacts rod 108, rod 108 pushes down on internal sleeve 405. As the downward rotation of set screw 122 continues, if internal sleeve 405 is in the upper position in anchor head 104, internal sleeve 405 moves downward within anchor head 104 compressing and ultimately crush-locking collet 407 around the head of pedicle screw 106, locking pedicle screw 106 with respect to anchor head 104. As shown in FIG. 8, internal sleeve has a bottom interior surface 455 preferably tapered inward by preferably about 30° so as to mate with the tapered tabs 427 of collet 407. Set screw 122 may be driven downward until (1) retention tabs 415a,b of sleeve 405 contact the bottom of slots 154a,b on anchor head 104, (2) the bottom edge 445 of sleeve 405 and lip 417 of collet 407 are clamped against internal ledge 144 of anchor head 104, and/or (3) tabs 427 are compressed against the head of the pedicle screw such that the sleeve can no longer travel down the bore of the anchor head. The set screw will push the spinal rod into the bottom of the U-shaped channel in sleeve 405 in order to move the sleeve down the bore of the anchor head. Once the sleeve can no longer move the sleeve down the bore of the anchor head, the set screw will apply pressure to the spinal rod so that it becomes locked in a final position in the sleeve (and in anchor head 104) so that the rod cannot slide and/or be removed from the anchor head.

Alternatively, other fasteners or caps may be used.

Collet 407 may be advantageously used with other types of anchor heads, internal sleeves, fasteners, and pedicle screws than those shown herein. For example, collet 407 may be used with similar corresponding bone anchor elements disclosed in the previously cited U.S. Provisional Patent Application No. 60/674,877, filed Apr. 25, 2005, incorporated herein by reference in its entirety.

FIGS. 9-11 show a second embodiment of a polyaxial bone anchor. Polyaxial bone anchor 900 includes fastener 102, an anchor head 904, and an anchor member 106. Anchor head 904 is substantially similar to anchor head 104 and is cylindrically hollow having a longitudinal bore 9014, top opening 9194, bottom opening 9184, and a generally U-shaped opening 903 transverse to the longitudinal bore for receiving spinal rod 108 or other similar part. Unlike anchor head 104, however, side lower portion 994 of anchor head 904 may have an inward taper. In one embodiment, side lower portion 994 may taper inward by about 0.65 mm on each side such that, for example, an upper width 924 of about 9.5 mm results in a lower width 9004 of about 8.2 mm. Bone anchor 100 may have the taper illustrated in this second embodiment and alternatively, bone anchor 900 may not have a taper as illustrated. Other representative dimensions of bone anchor 900 may be identical to those of bone anchor 100, and bone anchor 900 alternatively may be of other dimensions.

As with bone anchor 100, anchor member 106 (which will again be referred to hereinafter as pedicle screw 106) may be associated with or coupled to anchor head 904 such that the head and screw can polyaxially rotate with respect to each other. In particular, pedicle screw 106 can advantageously polyaxially rotate (before being locking or clamped in place) about central axis 909 of anchor head 904 by an angle θ of preferably about 50° in any direction (i.e., the angular rotation of the head of pedicle screw 106 in anchor head 904 forms a cone of preferably about 100°).

Figure 12:
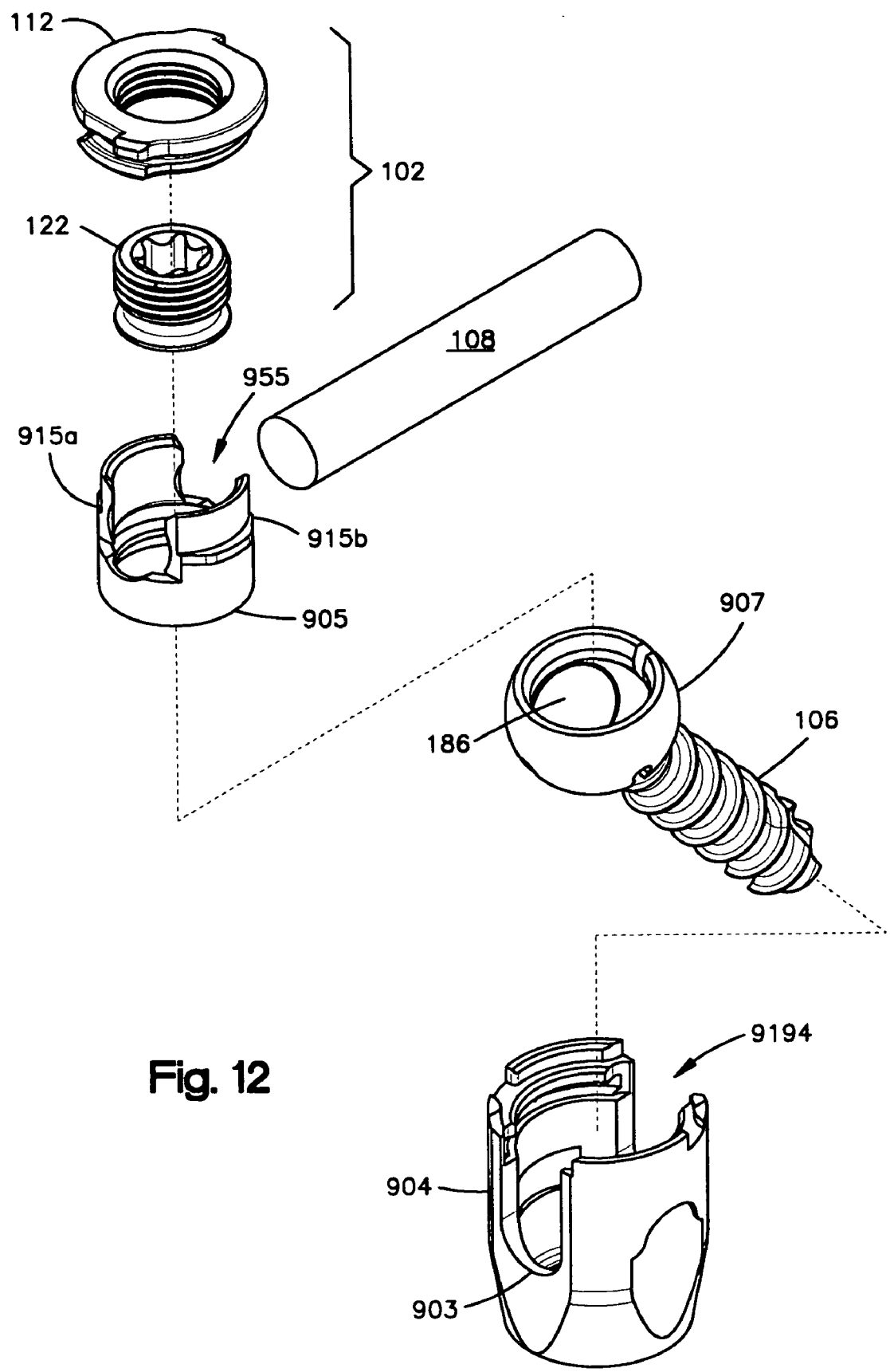
FIG. 12 is an exploded view of the polyaxial bone anchor of FIGS. 9-11.

FIG. 12 shows an exploded view of the assembly of bone anchor 900, which includes locking ring 112 and set screw 122 of locking cap 102, a hollow internal sleeve 905, spinal rod 108, an internal locking element 907, pedicle screw 106 (shown mounted in locking element 907), and anchor head 904. The assembly of bone anchor 900 is substantially, if not completely, identical to bone anchor 100. Locking element 907 is first snap-fitted onto the head 186 of pedicle screw 106. The locking element/screw assembly is then inserted screw-shank first through the top opening 9194 of anchor head 904 until the lower exterior surface 977 of locking element 907 rests against corresponding spherical inner surface 984 on the lower portion of anchor head 904. This causes screw shank 146 of pedicle screw 106 to protrude through the bottom opening 9184 of anchor head 904. Internal sleeve 905 may be inserted through top opening 9194 so that the sleeve is retained in anchor head 904.

As shown in FIGS. 12-15, locking element 907 may be described as a spherical bushing (referred to hereinafter as bushing 907). Bushing 907 is made of a resilient material that can be compressed around the head of pedicle screw 106 to retain pedicle screw 106 securely in place. Preferably the material of the bushing is softer than the material of internal sleeve 905 and pedicle screw 106. Internal space 917 of bushing 907 is shaped to substantially match the shape of the pedicle screw head such that the bushing has to be pressed over the screw head. Preferably, internal space 917 of the bushing has an arcuate or spherical shape to correspond to the preferably spherical or arcuate shape of the head of the pedicle screw. The exterior surface 987 of bushing 907 preferably has an arcuate or spherical shape. The inner surface 984 of lower portion 994 of anchor head 904 preferably has a corresponding arcuate or spherical shape so that bushing 907 can rotate or swivel in anchor head 904 about a point inside the anchor head and/or within the bore of the spherical bushing.

Figure 14:
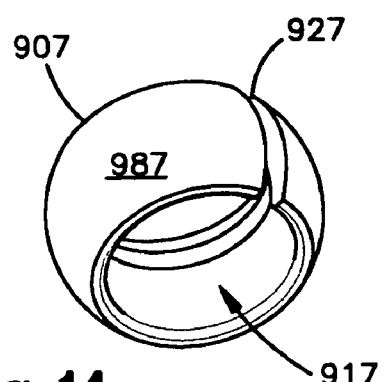
FIGS. 14 and 15 are perspective views of two embodiments, respectively, of the locking element of the polyaxial bone anchor of FIGS. 9-12.
Figure 15:
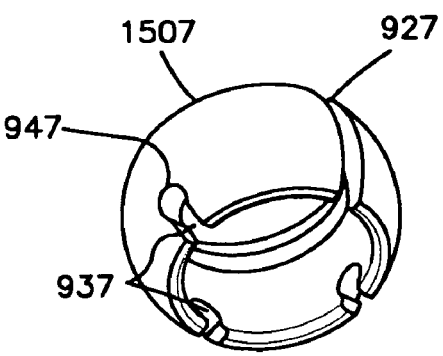
Figure 16:
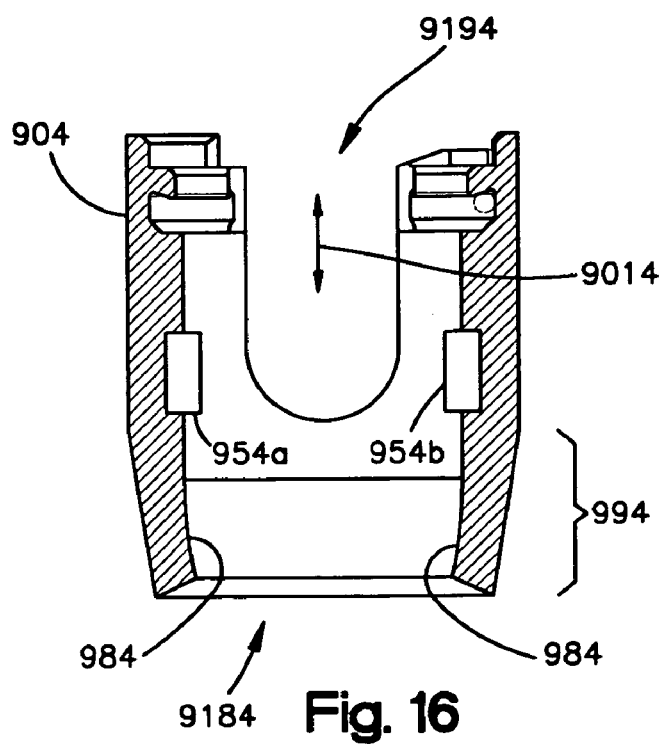
FIG. 16 is a side cross-sectional view of the anchor head of the polyaxial bone anchor of FIGS. 9-12.

Bushing 907 has a slot 927 to provide resiliency. Slot 927 may extend completely through from the exterior the side of bushing 907 to the interior side of the bushing and from the top end of the bushing to the bottom end of the bushing as shown in FIG. 14. Another embodiment of a spherical bushing according to the invention is shown in FIG. 15. Bushing 1507 has additional slots 937 that do not extend completely from the top end of the bushing to the bottom end of bushing 1507. Slots 937 may also have a radius or circular shaped portion 947 as a stress relief and/or to provide better resiliency. The arrangement, shapes, and dimensions of the slots of bushings 907/1507 alternatively may be different than shown. For example, although slots 937 are shown as extending from the lower or bottom end of bushing 1507, some or all of slots 937 alternatively can extend from the top end of bushing 1507.

Figure 13:
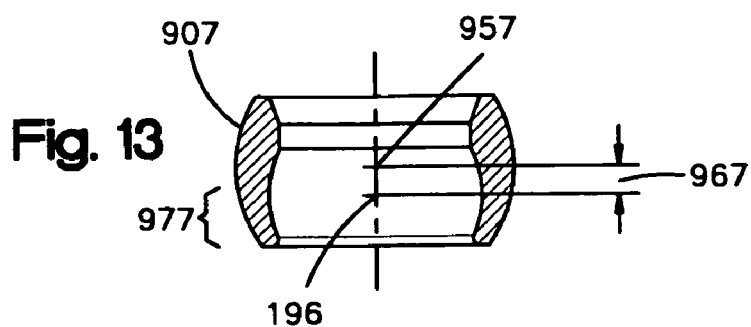
FIG. 13 is a cross-sectional view of the locking element of the polyaxial bone anchor of FIGS. 9-12.

Bushing 907 (and bushing 1507, referred to collectively hereinafter as bushing 907) can rotate or swivel about a point in the interior of the anchor head and/or bushing within anchor head 904 prior to locking. Inner surface 984 of anchor head 904 facilitates the rotation of bushing 907. As shown in FIG. 13, the inner surface of bushing 907 has a spherical centerpoint 957 that is preferably offset from the spherical centerpoint 196 of the exterior surface of bushing 907. This offset 967 is preferably about 0.6 mm (alternatively, offset 967 can be of other dimensions). In use, the pedicle screw may first angulate a certain amount until its shank 146 engages a lower edge 977 of bushing 907. At that point, bushing 907 can rotate with the pedicle screw to provide an additional amount of angulation, the sum of which provides the total angulation of the screw within the anchor head. The angulation of the screw within the bushing is preferably up to about 20° to about 30° of movement and the angulation of the bushing within the anchor head is preferably up to about 20° to about 30° of movement.

Alternatively, the centerpoints of bushing 907 and the pedicle screw head can be the same, which may maximize the retention capability of bushing 907 with respect to the screw head.

As with bone anchor 100, internal sleeve 905, which may be optional, is next inserted downward into anchor head 904. Internal sleeve 905 is positioned on top of bushing 907 and its insertion into and movement within anchor head 904 is substantially identical to that of internal sleeve 405 and anchor head 104. That is, internal sleeve 905 has a pair of retention tabs 915a,b on its outer surface that snap into respective slots 954a,b on opposite walls of anchor head 904. This insertion aligns the U-shaped channels of anchor head 904 and sleeve 905. Slots 954a,b of anchor head 904 allow sleeve 905 to move up and down from an unlocked screw position to a locked screw position, respectively. The sleeve may have the provisional locking features as described for bone anchor 100. Alternatively, other means of keeping U-shaped channel 955 of sleeve 905 aligned with U-shaped opening 903 in anchor head 904 may used, such as, for example, protruding tabs along the boundary of U-shaped channel 955 that project or snap into space provided by the U-shaped opening in anchor head 904.

With fastener 102 removed, the pedicle screw may be implanted in a bone, such as, for example, a vertebra, and anchor head 904 can thereafter be aligned to receive a spinal rod 108, which is snapped into internal sleeve 905 in a substantially, if not completely, identical manner as the corresponding parts of bone anchor 100.

Figure 17:
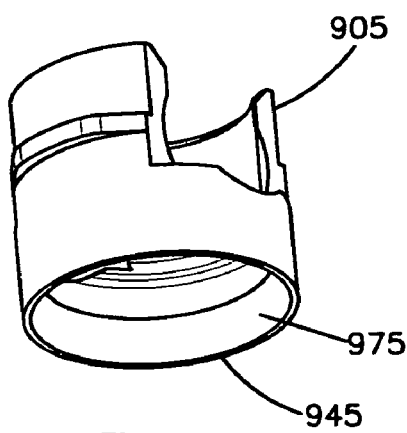
FIG. 17 is a perspective view showing the bottom of the internal sleeve of the polyaxial bone anchor of FIGS. 9-12.

Locking cap 102 is next placed on anchor head 904 and tightened to lock the rod and screw positions in a manner identical to that described above with respect to bone anchor 100. In particular, as set screw 122 contacts rod 108, rod 108 pushes down on internal sleeve 905. This causes internal sleeve 905 to move downward, compression locking bushing 907 against the head of pedicle screw 106. As shown in FIG. 17, internal sleeve 905 has a bottom surface 975 with a preferably corresponding arcuate or spherical shape that mates with the top portion of bushing 907. As with bone anchor 100, set screw 122 may be driven downward until retention tabs 915a,b of sleeve 905 contact the bottom of slots 954a,b on anchor head 904, until the bottom edge 945 of sleeve 905 and bushing 907 are clamped against surface 984 of anchor head 904, or until sleeve 905 contacts bushing 907 so that further movement of sleeve 905 is not possible. Alternatively, other fasteners or caps may be used.

As with collet 407, bushing 907 may be advantageously used with other types of anchor heads, internal sleeves, fasteners, and pedicle screws than those shown herein. Bushing 907 may be used with similar corresponding bone anchor elements disclosed in the previously cited International Patent Application PCT/US2006/015692, internationally filed Apr. 25, 2006, incorporated herein by reference in its entirety. Bushing 907 provides an additional degree of freedom as compared to collet 407. Bushing 907 not only will rotate about the longitudinal axis extending through the bore of the anchor head, but will rotate about an axis extending transverse to the longitudinal axis.

The present invention has been described in connection with the preferred embodiments. These embodiments, however, are merely for example and the invention is not restricted thereto. It will be understood by those skilled in the art that other variations and modifications can easily be made within the scope of the invention as defined by the appended claims, thus it is only intended that the present invention be limited by the following claims.

We claim:

1. A polyaxial bone anchor for rigidly attaching a rod to a bone, the bone anchor comprising:
an anchor head comprising a longitudinal bore having a top opening and a bottom opening, a channel transverse to the longitudinal bore for receiving the rod, and a central axis extending through the anchor head, the anchor head including an inner spherical surface formed in a lower portion;
an anchor member for attaching to the bone, the anchor member consisting of a first end, a second end, a first portion for engaging a bone including the first end, and a second portion positioned adjacent to, adjoining and extending from the first portion to the second end wherein the second portion is generally spherical and substantially devoid of any projections;
a bushing received within the longitudinal bore formed in the lower portion of the anchor head, the bushing including a top end, a bottom end, an exterior spherical surface for interacting with the inner spherical surface formed in the anchor head, an internal space defining an inner spherical surface for mating with the spherical head portion of the anchor member and a slot extending from the top end to the bottom end and from the exterior spherical surface to the inner spherical surface, the slot rendering the bushing radially expandable for receiving the head portion of the anchor member and radially compressible for applying a force to the head portion of the anchor member, the bottom end of the bushing extending beyond the bottom opening formed in the anchor head, the inner spherical surface of the bushing has a spherical centerpoint and the exterior spherical surface of the bushing has a spherical centerpoint, the spherical centerpoint of the inner spherical surface being vertically displaced toward the bottom end relative to the spherical centerpoint of the exterior spherical surface;
a sleeve slidably received within the longitudinal bore formed in the anchor head, at least a portion of the sleeve located between the rod and the top end of the bushing; and
a fastener removably mountable to the anchor head, the anchor member operable between an unlocked position and a locked position, in the unlocked position the rod and the anchor member are moveable with respect to the anchor head and in the locked position, the fastener applies a downward force to the rod, which applies a downward force to the sleeve, which applies a downward force to the bushing causing the bushing to radially compress against the head portion of the anchor member to thereby secure a position of the anchor member with respect to the anchor head and a position of the rod with respect to the anchor head.

2. The polyaxial bone anchor of claim 1 wherein an angle at which the anchor member can angulate from the central axis in at least one direction is about 50 degrees.

3. The polyaxial bone anchor of claim 1 wherein an angulation of the anchor member about the central axis forms a cone of about 100 degrees.

4. The polyaxial bone anchor of claim 1 wherein the bushing is operative to rotate within the anchor head when the fastener is in the unlocked position.

5. The polyaxial bone anchor of claim 1 wherein:
the bushing comprises a lip extending around the perimeter of the bushing;
the anchor head has an interior groove in which the lip can be positioned; and
the bushing is capable of rotation within the anchor head with the lip positioned in the groove when the fastener is in the unlocked position.

6. The polyaxial bone anchor of claim 1 wherein the sleeve has a generally U-shaped channel for receiving the rod.

7. The polyaxial bone anchor of claim 6 wherein the bottom end of the sleeve has a contour that matches the contacted portion of the bushing.

8. The polyaxial bone anchor of claim 7 wherein the bottom contoured end of the sleeve is arcuate.

9. The polyaxial bone anchor of claim 7 wherein the bottom contoured end of the sleeve is tapered upward and inward with respect to the sleeve.

10. The polyaxial bone anchor of claim 1 wherein the spherical inner surface of the anchor head has a radius of curvature that matches a radius of curvature of the exterior spherical surface of the bushing.

11. The polyaxial bone anchor of claim 1 wherein the anchor member is a screw.

12. The polyaxial bone anchor of claim 1 wherein the fastener is a locking cap comprising a locking ring and a set screw.

13. A polyaxial bone anchor for rigidly attaching a rod to a bone, the bone anchor comprising:
- an anchor head comprising a longitudinal bore having a top opening and a bottom opening, a generally U-shaped channel transverse to the longitudinal bore for receiving the rod, and a central axis extending through the anchor head and the bottom opening;
- an anchor member for attaching to the bone, the anchor member consisting of a first end, a second end, a first portion for engaging a bone including the first end, and a second portion positioned adjacent to, adjoining and extending from the first portion to the second end wherein the second portion is generally spherical and substantially devoid of any projections,
- a locking member received within the longitudinal bore formed in the anchor head, the locking member including a top end, a bottom end, an exterior spherical surface for interacting with the anchor head and an internal space defining an inner spherical surface for receiving the first portion of the anchor member, the second portion of the anchor member extending through the bottom opening of the anchor head, the inner spherical surface of the locking element has a spherical centerpoint and the exterior spherical surface of the locking element has a spherical centerpoint, the spherical centerpoint of the inner spherical surface being vertically offset toward the bottom end relative to the spherical centerpoint of the exterior spherical surface; and
- a fastener removably mountable to the anchor head to close the top opening of the longitudinal bore, the fastener is movable between an unlocked position and a locked position, in the unlocked position the rod and the anchor member are moveable with respect to the anchor head and in the locked position, the fastener applies a downward force to the rod to thereby rigidly secure a position of the anchor member with respect to the anchor head and a position of the rod with respect to the anchor head.

14. The polyaxial bone anchor of claim 13 wherein an angle at which the anchor member can angulate from the central axis in at least one direction exceeds 50 degrees.

15. The polyaxial bone anchor of claim 13 wherein an angulation of the anchor member about the central axis forms a cone of about 100 degrees.

16. The polyaxial bone anchor of claim 13 wherein the locking member is operative to rotate within the anchor head when the fastener is in the unlocked position.

17. The polyaxial bone anchor of claim 13 further comprising a hollow sleeve having a generally U-shaped channel for receiving the rod, the sleeve retained within the anchor head.

18. The polyaxial bone anchor of claim 17 wherein the sleeve has a bottom surface that engages a portion of the top end of the locking member, the bottom surface having a contour that matches the engaged portion of the top end of the locking member.

19. The polyaxial bone anchor of claim 18 wherein the bottom contoured surface of the sleeve is arcuate.

20. The polyaxial bone anchor of claim 18 wherein the bottom contoured surface of the sleeve is tapered upward and inward with respect to the sleeve.

21. The polyaxial bone anchor of claim 13 wherein the anchor head has an interior spherical surface around the bottom opening that engages a portion of the exterior spherical surface of the locking member and matches the contour thereof.

22. The polyaxial bone anchor of claim 13 wherein the anchor member is a screw.

23. The polyaxial bone anchor of claim 13 wherein the fastener is a locking cap comprising a locking ring and a set screw.

24. A polyaxial bone anchor for rigidly attaching a rod to a bone, the bone anchor comprising:
- an anchor head comprising a longitudinal bore having a top opening and a bottom opening, a channel transverse to the longitudinal bore for receiving the rod, and a central axis extending through the anchor head, the anchor head including an inner spherical surface formed in a lower portion;
- an anchor member for attaching to the bone, the anchor member including a generally spherically shaped upper head portion receivable within the anchor head, and a lower portion extending from the generally spherically shaped head portion for engaging bone;
- a bushing received within the longitudinal bore formed in the lower portion of the anchor head, the bushing including a top end, a bottom end, an exterior spherical surface for interacting with the inner spherical surface formed in the anchor head, an internal space defining an inner spherical surface for mating with the generally spherically-shaped head portion of the anchor member and a slot extending from the top end to the bottom end and from the exterior spherical surface to the inner spherical surface, the slot rendering the bushing radially expandable for receiving the head portion of the anchor member and radially compressible for applying a force to the head portion of the anchor member, the bottom end of the bushing extending beyond the bottom opening formed in the anchor head, the inner spherical surface of the bushing has a spherical centerpoint and the exterior spherical surface of the bushing has a spherical centerpoint, the spherical centerpoint of the inner spherical surface being vertically displaced toward the bottom end relative to the spherical centerpoint of the exterior spherical surface;
- a sleeve slidably received within the longitudinal bore formed in the anchor head, at least a portion of the sleeve located between the rod and the top end of the bushing; and
- a fastener removably mountable to the anchor head, wherein the anchor member is operable between an unlocked position and a locked position, in the unlocked position the rod, the anchor member and the bushing are movable with respect to the anchor head, the generally spherically shaped head portion of the anchor member rotatable within the inner spherical surface of the bushing and the exterior spherical surface of the bushing is rotatable within the inner spherical portion formed in the lower portion of the anchor head, and in the locked position the anchor member is rigidly and non-elastically fixed with respect to at least one of the anchor head and the bushing.

25. The polyaxial bone anchor of claim 24, wherein in the locked position the anchor member is rigidly and non-elastically fixed with respect to both the anchor head and the bushing.

26. The polyaxial bone anchor of claim 24 wherein an angle at which the anchor member can angulate from the central axis in at least one direction is about 50 degrees.

27. The polyaxial bone anchor of claim 24 wherein an angulation of the anchor member about the central axis forms a cone of about 100 degrees.

28. The polyaxial bone anchor of claim 24 wherein the bushing is operative to rotate within the anchor head when the fastener is in the unlocked position.

29. The polyaxial bone anchor of claim 24 wherein:
the bushing comprises a lip extending around the perimeter of the bushing;
the anchor head has an interior groove in which the lip can be positioned; and
the bushing is capable of rotation within the anchor head with the lip positioned in the groove when the fastener is in the unlocked screw position.

30. The polyaxial bone anchor of claim 24 wherein the sleeve has a generally U-shaped channel for receiving the rod.

31. The polyaxial bone anchor of claim 30 wherein the bottom end of the sleeve has a contour that matches the contacted portion of the bushing.

32. The polyaxial bone anchor of claim 31 wherein the bottom contoured end of the sleeve is arcuate.

33. The polyaxial bone anchor of claim 31 wherein the bottom contoured end of the sleeve is tapered upward and inward with respect to the sleeve.

34. The polyaxial bone anchor of claim 24 wherein the spherical inner surface of the anchor head has a radius of curvature that matches a radius of curvature of the exterior spherical surface of the bushing.

35. The polyaxial bone anchor of claim 24 wherein the anchor member is a screw.

36. The polyaxial bone anchor of claim 24 wherein the fastener is a locking cap comprising a locking ring and a set screw.

37. The polyaxial bone anchor of claim 24 wherein substantially the entire inner spherical surface of the bushing is approximately equal to the generally spherically shaped head portion.

38. The polyaxial bone anchor of claim 24 wherein in the locked position the anchor member is rigidly lockable at a non-orthogonal angle with respect to the bottom end surface of the bushing.

39. The polyaxial bone anchor of claim 24 wherein in the unlocked position the anchor member is symmetrically angularly adjustable about two points of rotation.

40. A polyaxial bone anchor for rigidly attaching a rod to a bone, the bone anchor comprising:
an anchor head comprising a longitudinal bore having a top opening, a bottom opening, a channel transverse to the longitudinal bore for receiving the rod, and a central axis extending through the anchor head, the anchor head including an inner spherical surface formed in a lower portion;
an anchor member for attaching to the bone, the anchor member including a generally spherically shaped upper head portion receivable within the anchor head, and a lower portion extending from the generally spherically shaped head portion for engaging bone;
a bushing received within the longitudinal bore formed in the lower portion of the anchor head, the bushing including a top end, a bottom end, an exterior spherical surface for interacting with the inner spherical surface formed in the anchor head, an internal space defining an inner spherical surface for mating with the generally spherically-shaped head portion of the anchor member and a slot extending from the top end to the bottom end and from the exterior spherical surface to the inner spherical surface, the slot rendering the bushing radially expandable for receiving the head portion of the anchor member and radially compressible for applying a force to the head portion of the anchor member, the bottom end of the bushing extending beyond the bottom opening formed in the anchor head, the inner spherical surface of the bushing has a spherical centerpoint and the exterior spherical surface of the bushing has a spherical centerpoint, the spherical centerpoint of the inner spherical surface being vertically displaced toward the bottom end relative to the spherical centerpoint of the exterior spherical surface;
a sleeve slidably received within the longitudinal bore formed in the anchor head, at least a portion of the sleeve located between the rod and the top end of the bushing; and
a fastener removably mountable to the anchor head, wherein the fastener is movable between an unlocked position and a locked position, wherein in the unlocked position the anchor member is symmetrically angularly adjustable, wherein an angulation of the anchor member about the central axis forms a cone of about 100 degrees.

41. The polyaxial bone anchor of claim 40, wherein in the locked position the anchor member is rigidly and non-elastically fixed with respect to both the anchor head and the bushing.

42. The polyaxial bone anchor of claim 40 wherein the bushing is operative to rotate within the anchor head when the fastener is in the unlocked position.

43. The polyaxial bone anchor of claim 40 wherein:
the bushing comprises a lip extending around the perimeter of the bushing;
the anchor head has an interior groove in which the lip can be positioned; and
the bushing is capable of rotation within the anchor head with the lip positioned in the groove when the fastener is in the unlocked screw position.

44. The polyaxial bone anchor of claim 40 wherein the bottom end of the sleeve has a contour that matches the contacted portion of the bushing.

45. The polyaxial bone anchor of claim 44 wherein the bottom contoured end of the sleeve is arcuate.

46. The polyaxial bone anchor of claim 44 wherein the bottom contoured end of the sleeve is tapered upward and inward with respect to the sleeve.

47. The polyaxial bone anchor of claim 40 wherein the spherical inner surface of the anchor head has a radius of curvature that matches a radius of curvature of the exterior spherical surface of the bushing.

48. The polyaxial bone anchor of claim 40 wherein the anchor member is a screw.

49. The polyaxial bone anchor of claim 40 wherein the fastener is a locking cap comprising a locking ring and a set screw.

50. The polyaxial bone anchor of claim 40 wherein substantially the entire inner spherical surface of the bushing is approximately equal to the generally spherically shaped head portion.

51. The polyaxial bone anchor of claim 40 wherein in the locked position the anchor member is rigidly lockable at a non-orthogonal angle with respect to the bottom end surface of the bushing.

52. The polyaxial bone anchor of claim 40 wherein in the unlocked position the anchor member is symmetrically angularly adjustable about two points of rotation.

53. A polyaxial bone anchor for rigidly attaching a rod to a bone, the bone anchor comprising:

an anchor head comprising a longitudinal bore having a top opening and a bottom opening, a channel transverse to the longitudinal bore for receiving the rod, and a central axis extending through the anchor head, the anchor head including an inner spherical surface formed in a lower portion;

an anchor member for attaching to the bone, the anchor member including a generally spherically shaped upper head portion receivable within the anchor head, and a lower portion extending from the generally spherically shaped head portion for engaging bone;

a bushing received within the longitudinal bore formed in the lower portion of the anchor head, the bushing including a top end, a bottom end, an exterior spherical surface for interacting with the inner spherical surface formed in the anchor head, an internal space defining an inner spherical surface for mating with the generally spherically-shaped head portion of the anchor member and a slot extending from the top end to the bottom end and from the exterior spherical surface to the inner spherical surface, the slot rendering the bushing radially expandable for receiving the head portion of the anchor member and radially compressible for applying a force to the head portion of the anchor member, the bottom end of the bushing extending beyond the bottom opening formed in the anchor head, the inner spherical surface of the bushing has a spherical centerpoint and the exterior spherical surface of the bushing has a spherical centerpoint, the spherical centerpoint of the inner spherical surface being vertically displaced toward the bottom end relative to the spherical centerpoint of the exterior spherical surface;

a sleeve slidably received within the longitudinal bore formed in the anchor head, at least a portion of the sleeve located between the rod and the top end of the bushing; and a fastener removably mountable to the anchor head, the anchor member operable between an unlocked position and a locked position, in the unlocked position the rod, the anchor member and the bushing are movable with respect to the anchor head, the anchor member being symmetrically angularly adjustable about two points of rotation.

54. The polyaxial bone anchor of claim 53, wherein in the locked position the anchor member is rigidly and non-elastically fixed with respect to both the anchor head and the bushing.

55. The polyaxial bone anchor of claim 53 wherein an angle at which the anchor member can angulate from the central axis in at least one direction is about 50 degrees.

56. The polyaxial bone anchor of claim 53 wherein an angulation of the anchor member about the central axis forms a cone of about 100 degrees.

57. The polyaxial bone anchor of claim 53 wherein the bushing is operative to rotate within the anchor head when the fastener is in the unlocked position.

58. The polyaxial bone anchor of claim 53 wherein:
the bushing comprises a lip extending around the perimeter of the bushing;
the anchor head has an interior groove in which the lip can be positioned; and
the bushing is capable of rotation within the anchor head with the lip positioned in the groove when the fastener is in the unlocked screw position.

59. The polyaxial bone anchor of claim 54 wherein the sleeve has a generally U-shaped channel for receiving the rod.

60. The polyaxial bone anchor of claim 59 wherein the bottom end of the sleeve has a contour that matches the contacted portion of the bushing.

61. The polyaxial bone anchor of claim 60 wherein the bottom contoured end of the sleeve is arcuate.

62. The polyaxial bone anchor of claim 60 wherein the bottom contoured end of the sleeve is tapered upward and inward with respect to the sleeve.

63. The polyaxial bone anchor of claim 53 wherein the spherical inner surface of the anchor head has a radius of curvature that matches a radius of curvature of the exterior spherical surface of the bushing.

64. The polyaxial bone anchor of claim 53 wherein the anchor member is a screw.

65. The polyaxial bone anchor of claim 53 wherein the fastener is a locking cap comprising a locking ring and a set screw.

66. The polyaxial bone anchor of claim 53 wherein substantially the entire inner spherical surface of the bushing is approximately equal to the generally spherically shaped head portion.

67. The polyaxial bone anchor of claim 53 wherein in the locked position the anchor member is rigidly lockable at a non-orthogonal angle with respect to the bottom end surface of the bushing.

* * * * *